US006203491B1

(12) United States Patent
Uribe

(10) Patent No.: US 6,203,491 B1
(45) Date of Patent: Mar. 20, 2001

(54) ADULT SEXUAL APPARATUS

(76) Inventor: Richard M. Uribe, 4757 Sun Valley Rd., Del Mar, CA (US) 92014

(*) Notice: Subject to any disclaimer, the term of this patent is extended or adjusted under 35 U.S.C. 154(b) by 0 days.

(21) Appl. No.: 09/306,105

(22) Filed: May 6, 1999

(51) Int. Cl.[7] .......... A61F 5/00
(52) U.S. Cl. .......... 600/38
(58) Field of Search .......... 600/38, 39, 41; 128/883, 845

(56) References Cited

U.S. PATENT DOCUMENTS

| | | | |
|---|---|---|---|
| 879,534 | 2/1908 | Fraser . | |
| 934,240 | 9/1909 | Tunnessen . | |
| 995,600 | 6/1911 | Heyser . | |
| 1,067,346 | 7/1913 | Jorgensen . | |
| 5,690,604 | 11/1997 | Barnett | 600/38 |
| 5,782,243 | 7/1998 | Bisyak | 128/845 |

OTHER PUBLICATIONS

Adam and Eve Catalog: Mar. 18, 1997, Mini–Peter Water Gun, p. 9.*

Two page Information Material from Cords Unlimited, Inc. received on or about Jun. 2–4, 2000 at the Erotica L.A. Show in Los Angeles, California.

* cited by examiner

*Primary Examiner*—John P. Lacyk
(74) *Attorney, Agent, or Firm*—Brown, Martin, Haller & McClain

(57) ABSTRACT

An improved hands-free adult sexual apparatus or adult toy for use by women or men. The apparatus is secured onto the user, or the user's clothing or belt, in a harness-like assembly and is also partially restrained to a fixed object. In one embodiment, a dildo or other phallic device is secured to a supportive backing while elastic straps allow the user to comfortably utilize the invention. A restraining line partially secures movement of the dildo or phallic device while the user manipulates the elastic straps. In another embodiment, the phallic device has a lubricant chamber that is activated by a user controlled trigger to permit the user to add lubricant as desired to the phallic device. In another embodiment, the invention has instead a sheathing device for use by males.

14 Claims, 3 Drawing Sheets

ADULT SEXUAL APPARATUS

The field of the invention is adult sexual apparatus including novelty apparatus for personal use and apparatus for men or women with sexual problems, such as women with vaginal dryness problems. Phallic devices have been used for years by women who do not have a sex partner or women who wish to engage is safe sex practices. In addition, vaginal substitutes have also been used by males who do not have a female sex partner. The awareness of pervasive sexually transmitted diseases such as AIDS have made the use of adult sex toys more common because they may be used as a sex substitute in safe sex practices. In addition, couples may find that including sex toys in their romantic interludes can add to the sexual experience.

Conventional hand-held devices are bothersome and cumbersome to use. Frequently, the user's arms and hands can get tired. Conventional devices which are clamped into a position are too restrictive and may be dangerous if not used properly.

The present invention is an improvement over the conventional adult sex apparatus and includes both female and male embodiments. The invention can be used "hands-free" since the invention is secured to the user, or the user's clothing or belt, in a harness-like assembly and is also partially restrained to a fixed object. In one aspect, the inventor has found that the use of elastic straps allows the user to control both the range and intensity of movement of the dildo or sheathing device while avoiding the problems with the conventional devices. The user can watch television, talk on the phone or play video games while utilizing the present invention. In one embodiment, a phallic device has a lubricant chamber that is activated by the user to permit the user to add lubricant: as needed to the phallic device.

Thus, it is an object of the present invention to provide an improved sexual apparatus that overcome the problems with conventional appliances. Another object is to provide an improved sexual apparatus for women or men. Other and further objects will appear to those skilled in the art from the specification and drawings, whereby FIG. 1 is a perspective view of one embodiment of the invention;

FIG. 1*a* is a side view of the embodiment shown in FIG. 1 with a user shown;

Figure 1:
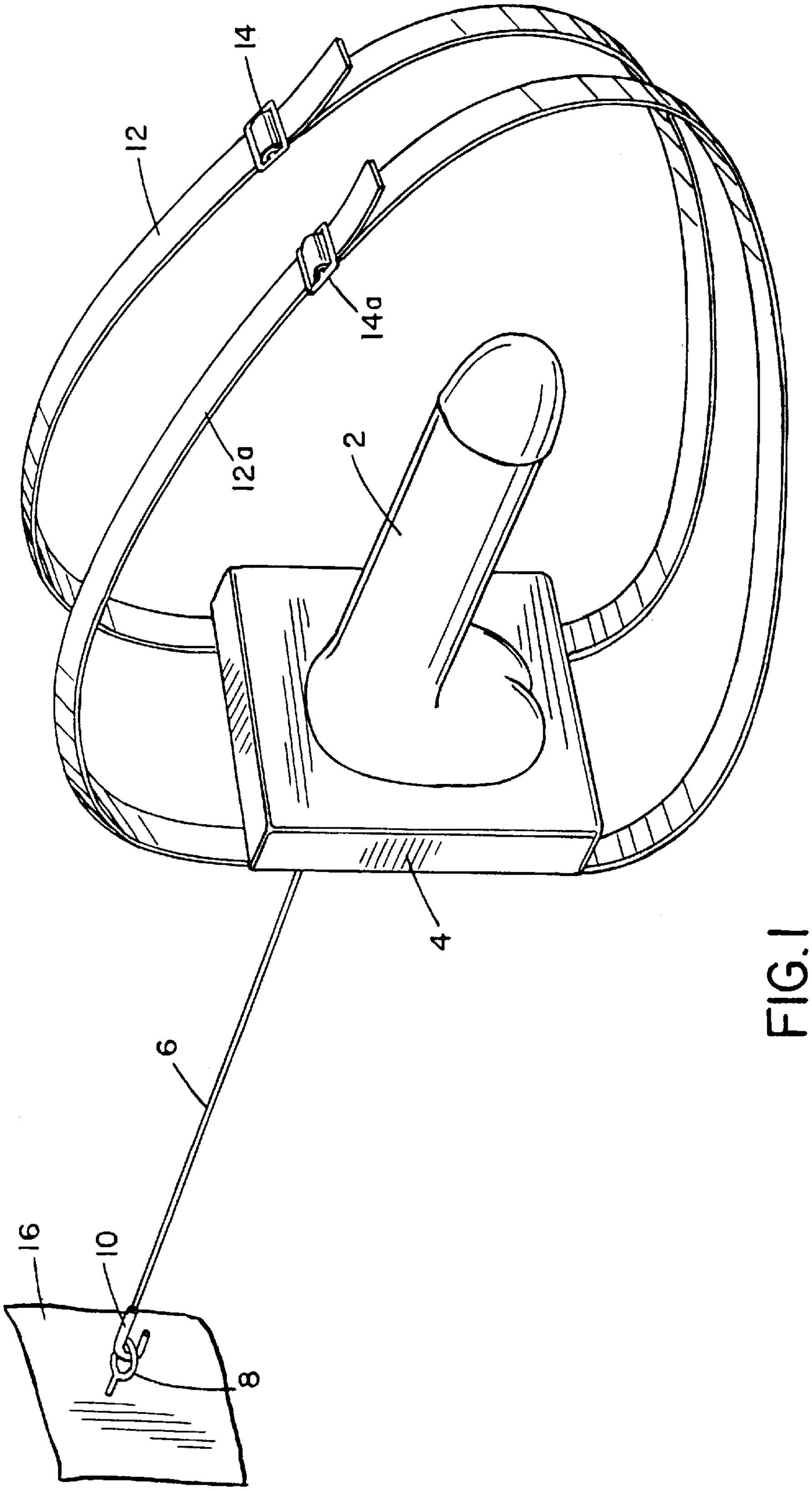

In a preferred embodiment, FIG. 1 shows one embodiment with the dildo 2 secured to a plastic backing 4, however any other type of support can be used for supporting the dildo 2. The dildo 2 may instead be any phallic device or penis substitute. The material used to make the dildo may preferably be V340 silicone resin with a RHODCA 45 catalyst, although other materials and compositions are within the scope of the invention. A restraining line 6 is also secured to the backing 4 and is preferably a rope or chain. An eye 8 may preferably attached to a fixed object 16 and a hook 10 secured to the other end of the restraining line 6 to temporarily secure the apparatus to a fixed object as shown in FIG. 1. Alternatively, the eye 8 may be secured to the end of the restraining line 6 and the hook 10 attached to the fixed object 16.

This embodiment has a pair of elastic straps 12 and 12*a* as shown in FIG. 1 which are preferably approximately two inches wide and preferably comprised of approximately 67% polyester and 33% rubber, although other compositions are within the scope of this invention. Also, the elastic straps 12 and 12*a* may have strap length adjustments 14 and 14*a* as shown in FIG. 1 to allow the user to custom fit the apparatus.

Figure 1A:
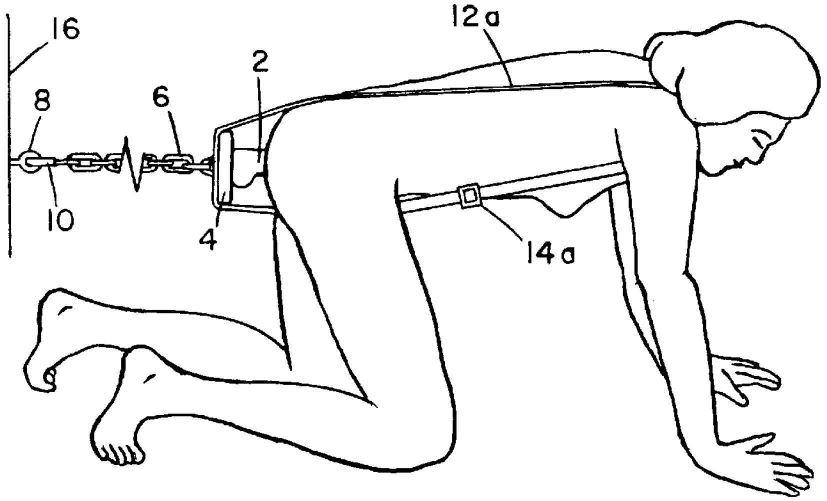

FIG. 1*a* shows the placement of this embodiment on the user. The strap length adjustments 14*a* and 14 may be used to create a snug fit on the user by manually adjusting their length. As shown in FIG. 1*a*, the restraining line 6 may be a chain having a hook 10 that may be removably secured to an eye 8 attached to a wall 16. The restraining line 6 is also secured to the plastic backing 4 at a securing point 18 (as pointed out in FIG. 2) which may be any conventional apparatus for attaching a chain or rope to a board or backing.

Figure 2:
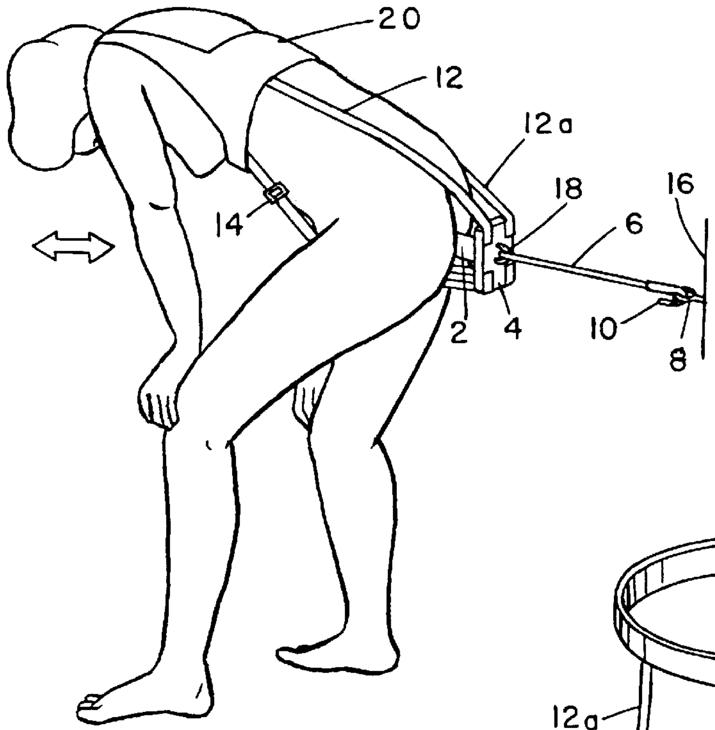
FIG. 2 is another perspective view of one embodiment showing the attachment to a vest worn by the user.

FIG. 2 shows another embodiment with the elastic straps 12 and 12*a* attached to a vest 20 worn by the user. The user in FIG. 2 is shown straddling the forward end of the dildo 2. As illustrated by the arrows in FIG. 2, user controlled stretching and then relaxing of the elastic straps 12 and 12*a* (in the direction of the arrows) urges the dildo 2 away from or into contact with the user's orifice, such as a vagina. The dildo 2 is at least partially restrained in the direction of the user's stretching movement by the restraining line 6 when the restraining line 6 is extended to its full length as shown in FIG. 2.

Figure 3:
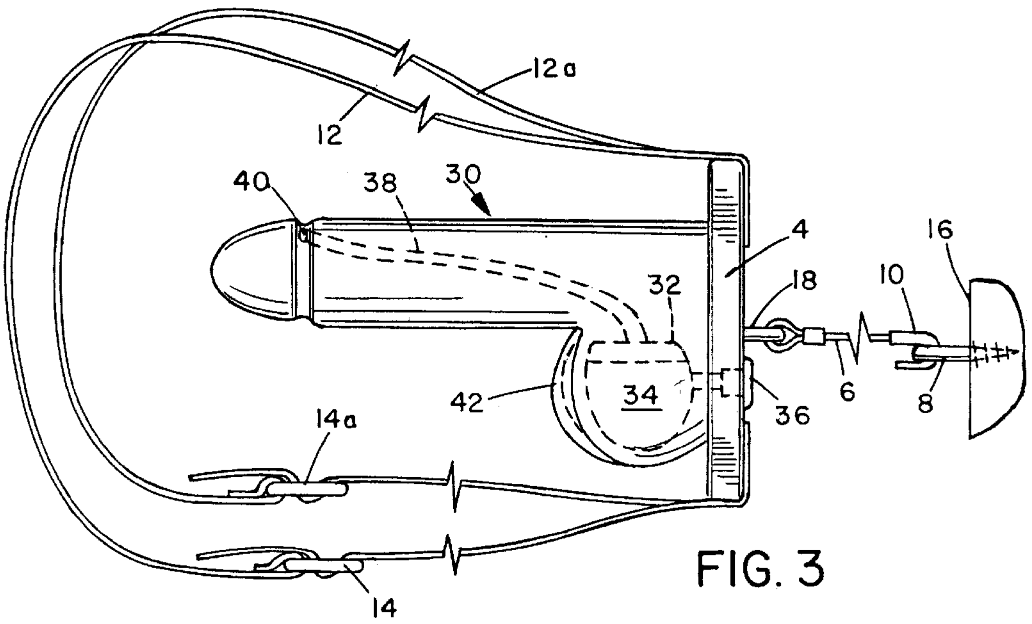
FIG. 3 is another embodiment of the invention showing a phallic device with a lubricant chamber.

In another embodiment, FIG. 3 shows a phallic device 30 with an internal lubricant chamber 32 for containing a volume of lubricant 34 as shown in FIG. 3. A plug 36 may preferably be used to seal the lubricant chamber 32 after it is filled with lubricant 34. A lubricant supply line 38 extends between the lubricant chamber 32 and the outlet 40 positioned on the exterior surface of the phallic device 30 preferably near the forward end of the phallic device 30 as shown in FIG. 3. However, other configurations with the outlet 40 at other positions on the phallic device 30 are included within the scope of the present invention.

Positioned adjacent to the lubricant chamber 32 is the lubricant supply trigger 42 In the preferred embodiment, the lubricant supply trigger 42 is manually depressed by the user which then causes the trigger 42 to compress or squeeze the lubricant chamber 32 which forces lubricant through the lubricant supply line 38 to the outlet 40 and onto the exterior of the phallic device 30. The lubricant supply trigger 42 is then released by the user and the above compressing or squeezing may be repeated by the user depending on the amount of lubricant 34 that is desired. The lubricant supply trigger 42 may be depressed by the user while the user is strapped into the present invention. The phallic device 30 may be used separately without the backing 4 and without the elastic straps 12 and 12*a*.

Figure 5:
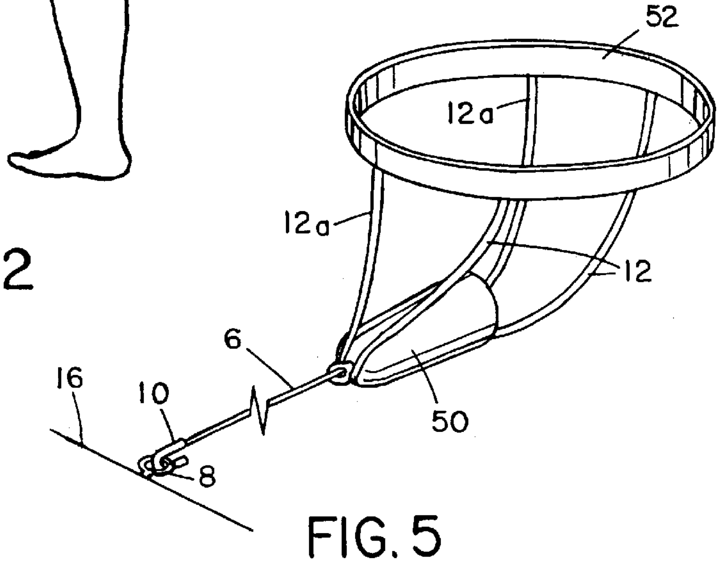
FIG. 5 is a side view of another male embodiment without the user shown.
Figure 4:
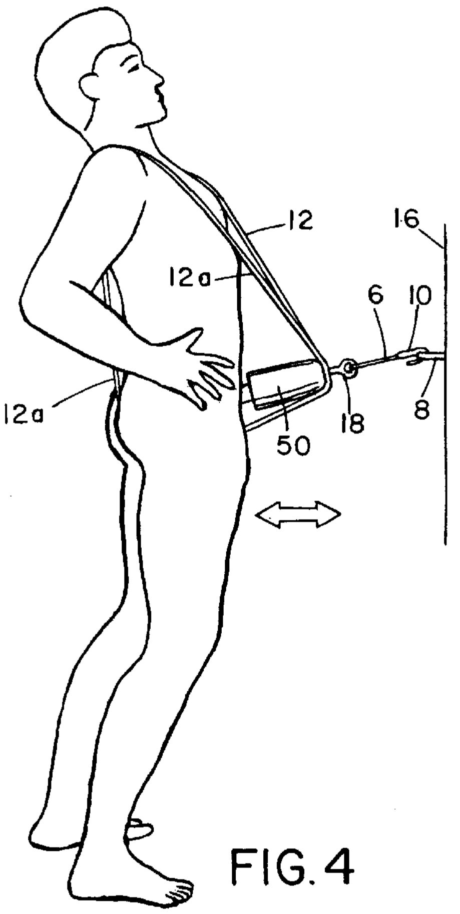
FIG. 4 is a side elevation view showing an embodiment of the present invention for males.
Figure 5A:
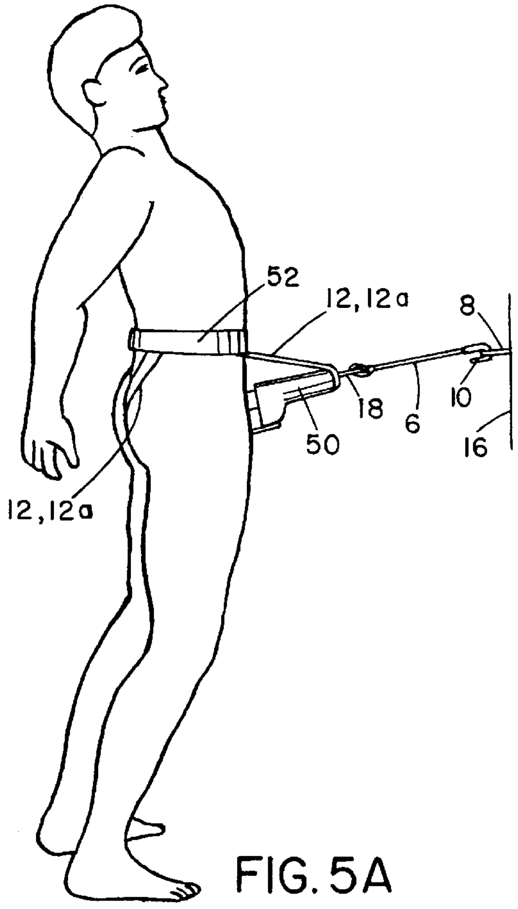
FIG. 5*a* is a side view of the male embodiment shown in FIG. 5 with the male user shown.

Another embodiment of the invention is shown in FIG. 4 for use by a male user. A sheathing device 50 is secured to the restraining line 6 which preferably has a hook 10 removably secured to an eye 8 as shown in FIG. 4. This embodiment also has the pair of elastic straps 12 and 12*a* which may include strap length adjustments 14 and 14*a* (as pointed out in FIG. 3) to allow the user to custom fit the apparatus. The straps 12 and 12*a* extend over the user's shoulders and between the user's legs as shown in FIG. 4. In FIG. 4, the user is shown straddling this embodiment with the sheathing device 50 placed over the user's penis. The user can choose to urge the sheathing device 50 over the user's penis by user-controlled stretching and relaxing of the elastic straps 12 and 12*a* in the direction of the arrows shown in FIG. 4. The sheathing device 50 is at least partially restrained in the direction of the user's stretching and relaxing movements by the restraining line 6 when the restraining line 6 is extended to its full length as shown in FIG. 4. The user can disengage the sheathing device 50 completely away from the user by stretching the elastic straps 12 and 12*a* in the direction away from the wall 12 as can be appreciated from FIG. 4. FIG. 5 shows another male embodiment with the elastic straps 12 and 12*a* secured to a belt 52 which may be worn by the user. FIG. 5*a* shows this embodiment as it may preferably be worn by the user.

While embodiments of the present invention and modifications thereto have been shown and disclosed in the drawings and specification, alternate embodiments of the present invention will be apparent to a person of ordinary skill in the art and this application is intended to include those embodiments within the full breadth and scope of the claims. The present invention is not limited by any parameters described herein and the present invention need not include all of the features disclosed in the single embodiment, but rather one or more features may be included.

What is claimed is:

1. An adult sexual apparatus, comprising:

a dildo having a forward end and a rearward end;

a restraining line having a first end attached adjacent to the rearward end of said dildo and adapted to partially restrain said dildo when said restraining line is extended; and elastic straps mounted adjacent to said dildo, said straps adapted to be removably secured to a user as the user straddles said forward end of said dildo and adapted to urge said dildo away from and into contact with the user's orifice, such as a vagina, by user-controlled stretching and relaxing of said elastic straps as said dildo is at least partially restrained by said restraining line.

2. The adult sexual apparatus of claim 1 where said dildo is a penis substitute.

3. The adult sexual apparatus of claim 1 where said dildo is a phallic device that includes lubricant supply means and manual trigger means for urging lubricant from said lubricant supply means to the outer surface of said phallic device.

4. The adult sexual apparatus of claim 2 where said penis substitute comprises:

a lubricant chamber;

a lubricant supply line between said chamber and the exterior surface of said penis substitute; and a lubricant supply trigger adapted to urge release of lubricant from said chamber through said supply line to the exterior of said penis substitute when said trigger is activated.

5. The adult sexual apparatus of claim 4 where said lubricant supply trigger is manually activated to urge lubricant from said chamber through said supply line.

6. The adult sexual apparatus of claim 1 where said returning line is a chain.

7. The adult sexual apparatus of claim 1 where said elastic straps are adapted to removably engage the shoulders of said user.

8. The adult sexual apparatus of claim 1 where said elastic straps are adapted to removably attach to a vest worn by said user.

9. The adult sexual apparatus of claim 1 where said elastic straps include strap length adjustments.

10. An improved adult male sexual apparatus, comprising:

a sheathing device;

a restraining line having a first end attached to said sheathing device and a second end adapted to partially restrain said sheathing device when said restraining line is extended; and elastic straps mounted adjacent to said sheathing device and adapted to be removably secured to a user as the user straddles said sheathing device for urging said sheathing device over the user's penis by user-controlled stretching and relaxing of said elastic straps and for user-controlled urging of said sheathing device away from said user by extending said restraining line.

11. The improved adult male sexual apparatus of claim 10 where said elastic straps removably engage the shoulders of said user.

12. The improved adult male sexual apparatus of claim 10 where said elastic straps removably attach to a vest worn by said user.

13. The improved adult male sexual apparatus of claim 10 where said elastic straps removably attach to a belt worn by said user.

14. The improved adult male sexual apparatus of claim 10 where said elastic straps include strap length adjustments.

* * * * *